United States Patent [19]

Preti et al.

[11] Patent Number: 4,772,559
[45] Date of Patent: Sep. 20, 1988

[54] METHOD OF DETECTING THE PRESENCE OF BRONCHOGENIC CARCINOMA BY ANALYSIS OF EXPIRED LUNG AIR

[75] Inventors: George Preti; John N. Labows, both of Horsham; Ronald Daniele, Philadelphia, all of Pa.; James G. Kostelc, Creve Coeur, Mo.

[73] Assignees: Monell Chemical Senses Center; University of Pennsylvania, both of Philadelphia, Pa.

[21] Appl. No.: 32,951

[22] Filed: Mar. 31, 1987

Related U.S. Application Data

[63] Continuation of Ser. No. 786,378, Oct. 10, 1985, abandoned.

[51] Int. Cl.$^4$ ............... G01N 33/00; G01N 33/48
[52] U.S. Cl. .................................. 436/64; 55/67; 128/719; 128/730; 436/96; 436/111; 436/140; 436/161; 436/813; 436/900
[58] Field of Search ............ 55/67; 128/716, 717, 128/719, 730; 436/64, 96, 111, 140, 161, 181, 813, 900

[56] References Cited

U.S. PATENT DOCUMENTS

| | | | |
|---|---|---|---|
| 3,236,601 | 2/1966 | Harvill | 436/111 |
| 3,444,239 | 5/1969 | Roberts | 436/161 X |
| 3,622,278 | 11/1971 | Elzinga et al. | 436/181 |
| 3,787,184 | 1/1974 | Novak et al. | 436/96 |
| 4,334,540 | 6/1982 | Preti et al. | 128/717 X |
| 4,349,626 | 9/1982 | Labows et al. | 435/38 |
| 4,359,323 | 11/1982 | LePage | 436/161 X |
| 4,534,360 | 8/1985 | Williams | 128/730 X |

OTHER PUBLICATIONS

Riehl et al., Rapid Detection of Aniline Vapors in Air, Analytical Chemistry, vol. 27, No. 11, Nov. 1955, pp. 1768 and 1769.
J. Zechman et al., "Volatile of *Pseudomonas aeruginosa* and Related Species by Automated Headspace Concentration-Gas Chromatography", *Can. J. Microbiol.*, 31; 232-237 (1985).
J. Brooks et al., "Analysis by Gas Chromatography of Hydroxyl Acids Produced by Several Species of Neisseria", *Canadian Journal of Microbiology*, 18: 157-168 (1972).
J. Brooks et al., "Further Studies on the Differentiation of *Clostridium sordellii* from *Clostridium bifermentans* by Gas Chromatography", *Canadian Journal of Microbiology*, 16: 1071-1078 (1970).
S. Chen et al., "Volatile Fatty Acids in the Breadth of Patients with Cirrhosis of the Liver", *Journal of Lab. Clin. Med.*, 75(4): 622-627 (Apr. 1970).
M. Simenhoff et al., "Biochemical Profile of Uremic Breath", *New England Journal of Medicine*, 297: 132-135 (Jul. 21, 1977).
B. Lorber, "'Bad Breath': Presenting Manifestation of Anaerobic Pulmonary Infection", *American Review of Respiratory Disease*, 112: 875-877 (1975).
Gori et al., "Etiology and Prevention of Cancer", *Preventive Medicine*, vol. 4, pp. 239-246 (1975).
Zlatkis et al., "The Role of Organic Volatile Profiles in Clinical Diagnosis", *Clinical Chemistry*, 27(6): 789-797 (1981).
Krotoszynski et al., "Characterization of Human Expired Air: A Promising Investigative and Diagnostic Technique", *Journal of Chromatographic Science*, vol. 15, pp. 239-244, Jul. 1977.
J. Brooks et al., "Analysis by Gas Chromatography of Fatty Acids Found in Whole Blood Cultural Extracts of Neisseria Species", *Canadian Journal of Microbiology*, 17: 531-543 (1971).
C. Moss et al., "Cellular Fatty Acids and Metabolic Products of Pseudomonas Species Obtained from Clinical Specimens", *Journal of Clinical Microbiology*, 4(6): 492-502 (1976).
T. Wade et al., "New Gas Chromatographic Characterization Procedure: Preliminary Studies on Some Pseudomonas Species", *Applied Microbiology*, 27(2): 303-311 (Feb. 1974).
A. Zlatkis et al., "Concentration and Analysis of Volatile Urinary Metabolites", *Journal of Chromatographic Science*, 11: 299-302 (Jun. 1973).
H. Liebich et al., "Volatile Substances in Blood Serum: Profile Analysis and Quantitative Determination", *Journal of Chromatography*, 142: 505-516 (1977).
J. Kostelc et al., "Quantitative Differences in Volatiles from Healthy Mouths and Mouths with Periodontitis", *Clinical Chemistry*, 27(6): 842-845 (1981).
E. Reiner et al., "Botulism: A Pyrolysis-Gas-Liquid Chromatographic Study", *Journal of Chromatographic Science*, 16: 623-629 (1978).
J. Kostelc et al., "Salivary Volatiles as Indicators of Periodontitis", *Journal of Periodontal Research*, 15: 185-192 (1980).
K. Matsumoto et al., "The Idendification of Volatile Compounds In Human Urine", *Journal of Chromatography*, 85: 31-34 (1973).
C. Patrianakos et al., "Chemical Studies on Tabacco Smoke LXIV. On the Analysis of Aromatic Amines in Cigarette Smoke", *J. of Analytical Toxicology*, 3: 150-154 (Jul./Aug., 1979).
H. Sakuma et al., "The Distribution of Cigarette Smoke Components Between Mainstream and Sidestream Smoke", *Beitrage zur Tabakforschung International*, 12(4): 199-209 (Jul. 1984).
D. Lane et al., "Real-Time Tracking of Industrial Emissions Through Populated Areas Using a Mobile APCI Mass Spectrometer System", *Advance Mass Spectrom*, 8B: 1480-1489 (1980).
I. McGregor et al., "Tinidazole in Smelly Oropharyngeal Tumors", *The Lancet*, p. 110 (Jan. 9, 1982).
S. Gordon et al., "Volatile Organic Compounds in Exhaled Air from Patients with Lung Cancer", *Clinical Chemistry*, 31: 1278-1282 (1985).

*Primary Examiner*—Robert Spitzer
*Attorney, Agent, or Firm*—Woodcock Washburn Kurtz Mackiewicz & Norris

[57] ABSTRACT

A novel method of detecting and diagnosing lung cancers by monitoring and analyzing expired lung air for the presence of selected aromatic amines, particularly aniline and ortho-toluidine, is provided.

10 Claims, No Drawings

METHOD OF DETECTING THE PRESENCE OF BRONCHOGENIC CARCINOMA BY ANALYSIS OF EXPIRED LUNG AIR

This is a continuation, of application Ser. No. 786,378, filed Oct. 10, 1985, now abandoned.

BACKGROUND OF THE INVENTION

The incidence of lung cancer in the United States is currently over 100,000 new cases per year and is expected to rise to nearly 300,000 by the year 2000. G. Gori and J. Peters, *Prev. Med.* 4:239-246 (1975). This expected increase is related both to the continued use of cigarettes and to exposure to various pollutants that exist in the work place and in urban home environments. More than two-thirds of the cases of bronchogenic carcinoma afflict middle-aged men, but the incidence among women is rising, and the proportion of female patients is expected to rise at an even greater rate as the effects of women's having entered the work place and begun smoking in increased numbers years ago are seen. The incidence today of lung cancer is 4-10 times greater in moderate cigarette smokers than in nonsmokers, and is 15-30 times greater in heavy smokers than in nonsmokers. The rising incidence is particularly alarming in view of the latent nature of this disease since the effect of exposure to a variety of substances found in industrial environments, such as asbestos, are just beginning to be seen.

Despite considerable efforts at early diagnosis and treatment, survival rates for bronchogenic carcinoma remain low. Although prognosis depends not only on cell type but also on the stage at which the disease is detected, the overall survival rate is still only about 10-25%. Recently, efforts have been made to more closely survey those individuals who fall into defined high-risk groups, such as those who smoke heavily or who are or have been chronically exposed to known carcinogens. Thus far, the most promising approach has been the screening of males of 45 years of age or older who have smoked at least 2 packs of cigarettes a day for 20 years. A combination of chest x-ray and pooled sputum analysis every four months has indicated lung cancers at an early stage of the disease, yielding a more favorable prognosis. More invasive methods of detecting the disease have been made, such as the use of fiber optic bronchoscopy, but these approaches have not significantly affected the rate of early diagnosis, which is still thought to be one of the most important considerations to long-term survival or ultimate cure.

The detection of other disease states by non-invasive methods has, so far, out-paced the use of such methods to detect lung cancer. Lung air, breath, and saliva are, for example, easily obtainable physiological samples that contain an array of volatile constituents whose presence has provided evidence of other systemic disease conditions or infection. The chemical identity of many volatile constituents, as well as their use in the study and diagnosis of diabetes, respiratory virile infection, and renal insufficiency has been described. A. Zlatkis, R. Brazell and C. Poole, *Clin. Chem.*, 27:789-797 (1981). Analysis of respiratory air by gas chromatography/mass spectrometry has shown the presence of simple endogenous alcohols, ketones, amines and numerous compounds of exogenous origin. B. Krotoszyinski, G. Gabriel and H. J. O'Neill, *Chrom. Sci.* 15:239 (1977). In several disease conditions, for example, specific volatile metabolites have been identified in breath samples, having been transferred into the aveolar air space from the blood. An example is the elevated levels of mercaptans and lower aliphatic acids found in the breath of patients with cirrhosis of the liver. S. Chen, V. Mahadevan and L. Zieve, *J. Lab. Clin. Med,* 75:622-27 (1970).

Monitoring the quantitative change in the presence of known indicators of disease or infection, over time, can indicate changes in physiological state, reflecting the advancement of the disease or the effect of treatment. For example, the classic uremic breath odor denotes the presence of dimethylamine and trimethylamine. M. Simenhoff, J. Burke, J. Saukkonen, A. Ordinario and R. Doty, *New England J. Med.*; 297:132-135 (1977) Gas chromatography/mass spectrometry analysis of breath volatiles, however, shows a marked reduction in the concentration of these amines following hemodialysis, demonstrating the relationship between lung air and blood for small organics and the use of sampling lung air to monitor treatment efficacy.

The detection of various other pathological states through the analysis of volatiles given off by various body samples is documented. High concentrations of acetone in breath samples of diabetics has been found. A. Zlatkis, R. Brazell and C. Poole, *Clin. Chem.*, 27:789-797 (1977). It has also been speculated that bacterial infections of the lung could be a further source of indicative volatiles present in expired lung air. B. Lorber, *Amer. Rev. Respiratory Dis.*, 112:875-877 (1975). U.S. Pat. No. 4,349,626 (issued Sept. 14, 1982, to Labows et al) discloses a method of detecting the presence of *Pseudomonas aeruginosa* through the analysis of characteristic volatile metabolites, such as various ketones and/or sulfur metabolites, associated with this infection. The disclosed detection method involves analyzing the volatiles in a head space over a sample of material associated with the site of the suspected infection, such as skin, sputum, breath, or saliva. U.S. Pat. No. 4,334,540 (issued June 15, 1982 to Preti et al) discloses a method of diagnosing periodontal disease through the detection of pyridine compounds in the headspace over, for example, breath or saliva samples.

The application of gas chromatography analysis techniques to the identification of unknown microorganisms is well known in general, and as described above, has been used in detection of various organic metabolites. See Zechman and Labows, "Volatiles of *Pseudomonas aeruginosa* and Related Species by Automated Headspace Concentration - Gas Chromatography," *Can. J. Microbiol* 31:232-237 (1985). The techniques which have been developed are based on analysis of either the unique metabolites of a given organism or on its individual structural components. Culture extracts have, for example, revealed specific amines for Clostridia (Brooks et al), "Further Studies on the Differentiation of *Clostridium sordelli* from *Clostridium bifermentans* by Gas Chromatography", *Can. J. Microbiol.*, 16:1071-8 (1970). Specific hydroxy acids and fatty acids have been identified for Neisseria. Brooks et al, "Analysis by Gas Chromatography of Hydroxy Acids Produced by Several Species of Neisseria", *Can. J. Microbiol.* 18:157-168 (1972); Brooks et al, "Analysis by Gas Chromatography of Fatty Acids Found in Whole Cultural Extracts of Neisseria Species", Can. J. Microbiol. 17:531-541 (1970). As mentioned above, bacteria cell wall preparations have been examined for unique fatty acid profiles, including such profiles for Pseudomonads. C. W. Moss, S. D. Dees, "Cellular Fatty Acid and Metabolic Products of Psuedomonas Species Obtained from Clincal Specimens", *J. Clin. Microbio.*, 4:492-502 (1976); and T. J. Wade, R. J. Mandel, "New Gas Chromatographic Characterization Procedure: Preliminary Studies on Some Pseudomonas Species", *Applied Microbio.*, 27:303-311, (Feb. 1974). Pyrolysis-gas chromatography of whole cell Clostridia bacteria has also been reported as giving identifiable differences in the observed fragmentation patterns. Reiner, et al, "Botulism: A Pyrolysis-Gas-Liquid Chromatographic Study", *J. Chromatogr. Sci.* 16:623-629 (1978).

Headspace analysis has also been applied to samples of human body fluids including saliva, urine, and blood serum. For references on this topic, please refer to Kostelc, et al, "Salivary Volatiles as Indicators of Periodontitis", *J. Periodont. Res.*, 18:185-192 (1980); Matsumota, et al, "Identification of Volatile Compounds in Human Urine", *J. Chromatogr.*, 85:31-34 (1973); Zlatkis, et al, "Concentration and Analysis of Volatile Urinary Metabolites", *J. Chromatogr. Sci.*, 11:299-302 (1973); Liebich, et al, "Volatile Substances in Blood Serum: Profile Analysis and Quantitative Determination", *J. Chromatogr.*, 142:505-516 (1977).

There remains a need for a non-invasive method for detecting the presence of lung cancer at an early stage, a method which, unlike the conventional invasive procedure, people will not be reluctant to undergo and which will thereby enhance early detection.

SUMMARY OF THE INVENTION

The present invention provides a novel method for screening an individual to determine whether there is an increased probability that he has brochogenic carcinoma. The method comprises the steps of (a) collecting a sample of expired lung air from that individual; and (b) presenting that sample to an indicator means which responds to at least one diagnostically indicative compound in that sample, whereby a positive response to said indicative compound diagnoses the existence of bronchogenic carcinoma.

Using sensitive analytical techniques, it has been found that people suffering from bronchogenic carcinoma (commonly, lung cancer) are more likely to produce certain distinctive compounds in their lungs which are present and detectable in expired air, and to produce those compounds in higher concentrations. People who do not suffer from this disease produce significantly lower or none of these compounds. In accordance with the present invention, an appropriate indicator means for sensing the presence of these compounds is used to test expired lung air. In a preferred embodiment of the invention, the compounds tested for are aniline and ortho-toluidine (2-methylaniline). The present method provides a non-invasive procedure for diagnosing lung cancers, particularly at an early stage when the prognosis is better, and as such can be used for screening, to detect lung cancers even before symptoms are discernible and therefore before the more invasive detection means conventionally used would be employed.

A preferred indicator for use in the present invention is a gas chromatograph (GC) and/or a GC combined with a mass spectrometer (GC/MS). To aid in the evaluation of the lung air sample, the GC may preferably be fitted with a nitrogen specific detector which will aid in identifying nitrogen-containing compounds, thereby more easily enabling one who analyzes the chromatograph-generated data to identify the presence of aniline or ortho-toluidine in the test substances.

Since the above-identified compounds are specifically related to the disease process, monitoring the presence and abundance of these compounds in lung air over a period of time serves further diagnostic functions: whether changes in the disease state have occurred, and if so, how the extent of those changes; and whether treatment has halted or reversed the disease process. As a result, a significant diagnostic tool is provided by the present invention which should enhance early detection and treatment of bronchogenic carcinoma.

DETAILED DESCRIPTION OF THE INVENTION

The present invention is a result of applicants' experimental confirmation that organic constituents of expired lung air are representative of organic compounds being produced in lung tissue and of volatiles in the blood which are in equilibrium with lung fluid and tissue. Volatile organic constituents of lung air are thought to be in equilibrium with a number of systems within the lung, and the presence of many of these constituents is attributed to endogenous or absorbed volatile substances circulating in the blood stream. In addition, certain substances in lung air may be in equilibrium with aveolar fluid or lining material. Finally, mucous glands and cells within the air spaces, tumor cells or cells which are attached to the bronchial epithelium, such as aveolar macrophages, may also contribute to the constituents of lung air.

The experimental confirmation of this invention was performed using gas chromatography (GC) and gas chromatography-mass spectrometry (GC/MS). These techniques have allowed the evaluation of a large number of volatile constituents whose relationship to the bronchial health of human subjects had previously been unexamined. The confirming tests have been conducted as described below.

A total of 16 control subjects were used in the study. Eight (age range 22-41) were recruited from the Interstitial Lung Disease Program at the Hospital of the University of Pennsylvania. Eight aged-matched control subjects (age range 57-66) were recruited from amongst employees of the Monell Center and the Skin Study Center of the University's Dermatology Department. These volunteers met the following criteria: (1) no symptoms of chronic or acute pulmonary disease; (2) no history of exposure to industrial dust or particulates; (3) normal chest x-ray; and (4) no medication at the time of the study. Among the control subjects, "non-smokers" were defined for purposes of this study as those who had abstained completely from tobacco products for at least five years. Those classified by this study as "smoking" control subjects were smoking between one-half and two packs of cigarettes per day, but did not exhibit symptoms of chronic bronchitis as defined by the American Thoracic Society.

Ten patients, suspected of having bronchogenic carcinoma, were drawn from the Pulmonary Clinic at the Hospital of the University of Pennsylvania. The patients were evaluated with respect to smoking history and with respect to exposure to suspected carcinogens in their industrial or occupational environments. This patient population included seven males, (aged 66, 68, 68, 77, 76, 63 and 70) and three females (aged 59, 62 and 54). All were or had been heavy smokers, although five of the male patients had stopped smoking over three years before the study. Each patient donated a sample of lung air on that patient's initial visit to the clinic, prior to diagnosis and treatment. Subsequent x-ray, bronchoscopy, and biopsy confirmed the diagnosis of either squamous cell carcinoma (6 patients), undifferentiated large cell carcinoma (2 patients) or adenocarcinoma (2 patients).

All participants in this study were asked to exhale end-expiratory air into a tube connected to a 20 liter Tedlar bag (Cole-Palmer Inc.). The bags were immediately returned to a laboratory and the contents transferred, by means of a vacuum pump, to a frosted glass collection tube containing 300 mg of Tenax, 60/80 mesh. Tenax is a porous organic polymer which absorbs organic constituents with little or no retention of water. It is available from the Applied Science Laboratory, State College, Pa. The collection tubes were sealed and frozen until analyzed.

GC and GC/MS were used to analyze the mixtures of these test substances. The organic materials collected on the Tenax traps were desorbed from the polymer by rapidly heating the collection tube to 240° C., and sweeping the volatiles in a helium stream over a 3 minute period into the first 15–20 cm of a nitrogen cooled chromatograph capillary column. Following this, the cooling apparatus was removed from the column, the collection tube was removed from the injection port, a carrier gas flow was resumed through the column, and the chromatograph's oven was brought to its starting temperature of 60° C.

A Finnegan 4510 GC/MS equipped with a split/splitless injector, a fused silica capillary column, and capability for operation in both electron impact and chemical ionization modes were used for the analysis. Components were separated on a CP Wax-57 CB column (25 meters×0.32 mm) with a 1.2 micron coating. The GC was programmed from 60° C. (with a 4 minute hold period) to 220° C. at 3°/minute. The spectrometer was connected to a Nova 3 computer, which utilizes software for data acquisition and analysis, including a library of 31,000 known compounds. The mass range of m/z 40–450 was scanned once each second and a typical run included 4000 1-second scans. Identifications were based on comparison of the unknown spectra with the 31,000 compound library and manual interpretation of the resulting comparison with mass spectra generated from commercially available standard compounds. In addition, the relative chromatographic retention times of unknown and known standards were compared. A series of C2-C18 fatty acid ethyl esters were used as relative retention time standards. In the case of the anilines, authentic samples were used for comparison of retention times (scan numbers), mass spectra and obtaining standard curves for quantitation.

Table 1 lists all the major compounds found in the combined study of the patient and control populations. The compounds in the table are divided into those thought to be of metabolic origin, those thought to be from exogenous sources (including food and environmental exposure), and those (three compounds) whose origins were not capable of probable categorization. The major components in the lung air from patients with lung carcinoma and control subjects (regardless of age) are qualitatively similar. However, differences in several minor components were discernible after careful examination of each peak in the reconstructed ion chromatograms generated by the collected lung air constituents.

TABLE 1

| Metabolic origin | |
|---|---|
| | Exogenous origin |
| isoprene | toluene |
| acetone | limonene |
| dimethyldisulfide | styrene |
| pyridine | octylacetate |
| acetoin | menthol |
| benzaldehyde | terpineol |
| hexanol | butylated hydroxytoluene |
| pentanone | benzothiazole |
| acetophenone | diphenylamine |
| cumene alcohol | iso-octanol |
| dodecanol | |
| phenol | Other |
| cresol | |
| indole | benzonitrile |
| | aniline |
| | o-toluidine |

Aniline and o-toluidine were initially found in the expired lung air of one carcinoma patient. Subsequently, the corresponding retention time window of chromatograms generated from all participants were searched for these compounds according to the key ions in their mass spectrum (m/z 93,66 for aniline; m/z 06,107 for o-toluidine). Aniline was found in 5 of the 10 cancer patients, none of the aged-matched controls (55–66 yrs), and 2 of the 8 younger (22–41 yrs) controls. Ortho-toluidine was found in of the 10 cancer patients, 3 of the 8 younger controls and 6 of 8 aged-matched controls. The level of o-toluidine found in the cancer patients was significantly higher than the level found in either control group and all but one of the 4 controls whose air samples did contain it. Table 2 summarizes the results of the analysis for the presence of aniline and o-toluidine in the control/patient population. The data in Table 2 were analyzed to determine if the levels of aniline and o-toluidine seen in controls was different than patients.

The data presented in Table 2 show that levels of aniline and o-toluidine will most likely be elevated in people with bronchogenic carcinoma. Ortho-toluidine was found in significantly elevated levels in patients with lung air when compared to either aged-matched (T=2.217; df=16; p<0.05) or younger controls (T=2.14; df=16; p<0.05). The highest levels of aniline were found in 4 of the 6 patients with squamous cell carcinoma suggesting a possible relationship between this cell type and production of the aniline. Consequently, levels of o-toluidine equal to or greater than the mean level of carcinoma patients in conjunction with measurable levels of aniline would suggest the increased probability of carcinoma.

TABLE 2

| | | | | | Presence of Aniline and O-Toluidine in Patient/Control Population | | |
|---|---|---|---|---|---|---|---|
| | Population | | | | | Concentration ng/20 L Lung Air | |
| Patient | Age | Sex | Smoking[1] | | Diagnosis[2] | Aniline | O-Toluidine |
| 1 | 66 | M | SS8; >30 pk yrs. | | Squamous Cell | 2.01 | 6.26 |

TABLE 2-continued
Presence of Aniline and O-Toluidine in Patient/Control Population

| Patient | Population Age | Sex | Smoking[1] | Diagnosis[2] | Concentration ng/20 L Lung Air Aniline | O-Toluidine |
|---|---|---|---|---|---|---|
| 2 | 59 | F | S; >40 pk yrs. | Squamous Cell | 17.56 | 9.55 |
| 3 | 68 | M | SS3; >40 pk yrs. | Squamous Cell | 13.87 | 19.45 |
| 4 | 68 | M | SS5; >40 pk yrs. | Squamous Cell | ND | 5.26 |
| 5 | 77 | M | SS10; >50 pk yrs. | Squamous Cell | 24.08 | 9.00 |
| 6 | 70 | M | S; >40 pk yrs. | Squamous Cell | ND | ND |
| 7 | 62 | F | SS1; >40 pk yrs. | Undiff. large cell | ND | 1.53 |
| 8 | 76 | M | SS15; >30 pk yrs. | Undiff. large cell | ND | 2.24 |
| 9 | 54 | F | S; >40 pk yrs. | Adenocarcinomia | 7.44 | 6.20 |
| 10 | 63 | M | S; >45 pk yrs. | Adenocarcinomia | ND | 8.77 |
| Age - Matched Controls (57-66) | | | | | | |
| AC1 | 66 | M | S; >45 pk yrs. | | ND | 0.181 |
| AC2 | 64 | M | S; >40 pk yrs. | | ND | 2.94 |
| AC3 | 57 | F | S; >25 pk yrs. | | ND | 4.30 |
| AC4 | 55 | M | S; >30 pk yrs. | | ND | 2.82 |
| AC5 | 54 | F | NS | | ND | 4.92 |
| AC6 | 58 | F | SS1; >40 pk yrs. | | ND | 2.94 |
| AC7 | 63 | F | NS | | ND | ND |
| AC8 | 59 | M | NS | | ND | ND |
| Young - Controls (22-41) | | | | | | |
| YC1 | 27 | F | S; >5 pk yrs | | ND | ND |
| YC2 | 24 | M | NS | | ND | ND |
| YC3 | 25 | F | S; >8 pk yrs. | | ND | ND |
| YC4 | 27 | F | NS | | ND | 2.80 |
| YC5 | 22 | F | NS | | 8.6 | ND |
| YC6 | 41 | F | SS6; >15 pk yrs. | | ND | ND |
| YC7 | 34 | F | S; >16 pk yrs. | | 5.89 | 11.05 |
| YC8 | 22 | F | NS | | ND | 0.88 |

[1]"S" = smoker; "NS" = non-smoker; "SSX" = stopped smoking x yrs prior to study; pk yrs = pack years
[2]Diagnosis by cell type which were either Squamous Cell Carcinoma; Undifferentiated Large Cell Carcinomia or Adenocarcinoma
[3]Quantitation is based on the amount recovered from 20 L bags. The efficiency of transfer of aniline and o-toluidine from the bags to gas chromatograph/mass spectometer system is approx. 10%; ND = not detected, below instrument detection threshold which is approximately 0.1 picograms.

The majority of compounds listed in Table 1 have already been reported by others, or are similar to those that have been reported by others, as being volatile constituents of either respiratory air or other body specimens. See, for example, A. Zlatkis, R. Brazell, and C. Poole, Clin. Chem., 27:289–297 (1981). B. Krotoszyinski, G. Gabriel and H. J. O'Neill, Chrom. Sci., 15:239 (1977). Many volatile nitrogen-containing compounds, such as heterocyclics (pyrroles, indole, pyridines, pyrollines), aliphatic amines, and benzylamine, which is a structural isomer of o-toluidine, are among the reported compounds identical to or similar to those of Table 1. Alkyl pyridines have been detected in headspace over human saliva and are believed to be a breakdown product of collagen. See J. Kostelc, P. Zelson, G. Preti and J. Tonzetich, Clin. Chem., 27:842–845 (1981). Menthol, although detected in the air samples obtained from several of the cancer patients, is a pervasive compound, being present in cigarettes as well as personal health and toiletry preparations, and consequently was thought to be exogenous rather than tumor-related.

Aniline, methylanilines, and N-ethyl and N,N-dimethyl-anilines have been reported in cigarette smoke. Specifically, levels of aniline and o-toluidine have been reported as 364 ng and 162 ng, respectively, in main stream cigarette smoke and considerably higher in sidestream cigarette smoke. See C. Patrianakos and D. J. Hoffmann, Anal. Toxic, 3:150–154 (1979). H. Sakuma, K. Kusama, K. Yamaguchi, T. Matsuki, and S. Sugawara, Beitrage Tabakforschung Int., 12:199–209 (1984). Nevertheless, aniline detected in this study in the lung air samples of the cancer patients, all of whom smoke, was not attributed to cigarettes since aniline was detected in only one of the five smoking control participants. Similarly, o-toluidine was detected in all four smoking cancer patients but in only three of the five smoking control participants; in two of those controls, the detected level of the compound was significantly lower than that in any of the cancer patients.

Aniline has been reported with diphenylamine and benzothiazole, to be present in various industrial emissions. See D. Lane, B. Thampson, A. Lovett and N. Reid, Adv. Mass Spectrom., 8B:1480–1489 (1980). However, diphenylamine and benzothiazole were found in all participants of this study, whereas aniline was not found in all but rather was present at a statistically significantly higher level in five of the cancer patients, particularly those with squamous cell carcinoma.

From the accumulation and analysis of this data, applicants have concluded that aniline and o-toluidine originate from a physiological process, not presently known, that is linked to bronchogenic tumor formation or growth. These anilines are not believed to be exogenous in origin, nor has the present study linked their presence to bacterial colonization of tumors, a phenomenom that has previously been reported. See I. McGregor, J. Watson, G. Sweeney and J. Sleigh, Lancet, I:110 (1982). Accordingly, the presence of aniline or o-toluidine in expired lung air at the concentration seen in the cancer patients described here is suggestive of bronchogenic carcinoma.

The preferred indicator means of this invention allows the screening of expired lung air to detect the presence of these two diagnostically indicative compounds at levels of parts per million or parts per billion. It is within the scope of the present invention, however, to use alternate indicator means which can be more or less sensitive than those described herein. For example, the organic constituents of the expired lung air sample can be detected and quantified using a variety of different methodologies, including colorometric and/or immunoreactive tests.

We claim:

1. A method for screening an individual to determine the probability of bronchogenic carcinoma in that individual comprising the steps of:
   (a) collecting a sample of expired lung air from that individual; and
   (b) presenting that sample to an indicator means which responds specifically to a diagnostically indicative compound in that sample, said indicative compound being selected from the group consisting of aniline and o-toluidine, whereby a positive response to said indicative compound indicates an increased probability of biochogenic carcinoma.

2. The method of claim 1 wherein step (b) comprises providing an indicator means responsive to aniline.

3. The method of claim 2 wherein said indicator means also respond quantitatively.

4. The method of claim 3 which further comprises the steps of (c) repeating steps (a) and (b); and (d) comparing the response from the later performed step (b) with the earlier performed step (b) to monitor a change in the disease state.

5. The method of claim 1 wherein step (b) comprises providing an indicator means responsive to o-toluidine.

6. The method of claim 5 wherein said indicator means also respond quantitatively.

7. The method of claim 1 wherein said indicator means also respond quantitatively to said indicative compound.

8. The method of claim 7 wherein said quantitative response is compared to normal control amounts, whereby a higher concentration of said compound is indicative of a higher probability of said carcinoma.

9. The method of claim 8 which further comprises the steps of (c) repeating steps (a) and (b); and (d) comparing the response from the later performed step (b) with the earlier performed step (b) to monitor a change in the disease state.

10. The method of claim 7 which further comprises the steps of (c) repeating steps (a) and (b); and (d) comparing the response from the later performed step (b) with the earlier performed step (b) to monitor a change in the disease state.

* * * * *